(12) United States Patent
Takeda et al.

(10) Patent No.: US 7,961,844 B2
(45) Date of Patent: Jun. 14, 2011

(54) ROTATING IRRADIATION THERAPY APPARATUS

(75) Inventors: Norio Takeda, Kashiwa (JP); Shigeji Kaneko, Hitachi (JP); Tsutomu Yamashita, Hitachi (JP); Hiroshi Saga, Takahagi (JP)

(73) Assignee: Hitachi, Ltd., Tokyo (JP)

( * ) Notice: Subject to any disclaimer, the term of this patent is extended or adjusted under 35 U.S.C. 154(b) by 287 days.

(21) Appl. No.: 12/438,029

(22) PCT Filed: Aug. 29, 2007

(86) PCT No.: PCT/JP2007/066791
§ 371 (c)(1),
(2), (4) Date: Feb. 19, 2009

(87) PCT Pub. No.: WO2008/026648
PCT Pub. Date: Mar. 6, 2008

(65) Prior Publication Data
US 2010/0163755 A1    Jul. 1, 2010

(30) Foreign Application Priority Data

Aug. 31, 2006  (JP) ................................ 2006-234860

(51) Int. Cl.
*A61N 5/10*    (2006.01)
*A61N 5/00*    (2006.01)
(52) U.S. Cl. .......................... 378/65; 378/64; 250/492.3

(58) Field of Classification Search ............... 250/491.1, 250/492.1, 492.3; 378/64, 65, 68, 195, 196, 378/197
See application file for complete search history.

(56) References Cited

U.S. PATENT DOCUMENTS 5,993,373 A * 11/1999 Nonaka et al. ..................... 600/1
6,897,451 B2 * 5/2005 Kaercher et al. .......... 250/396 R

FOREIGN PATENT DOCUMENTS

| JP | 51-34925 | 8/1976 |
| JP | 01-102290 | 4/1989 |
| JP | 11-047287 | 2/1999 |
| JP | 11-216195 | 8/1999 |
| JP | 2000-140134 | 5/2000 |
| JP | 3124553 | 10/2000 |
| JP | 2000-329471 | 11/2000 |
| JP | 2004-148103 | 5/2004 |

* cited by examiner

*Primary Examiner* — Bernard E Souw
(74) *Attorney, Agent, or Firm* — Mattingly & Malur, P.C.

(57) ABSTRACT

A rotating irradiation therapy apparatus used for particle beam therapy includes a rotating gantry equipped with a charged particle beam irradiation device beam transport devices for guiding a charged particle beam to the irradiation device and a roller in contact with a ring member included in the rotating gantry and supporting the gantry. A front ring is disposed in contact with the roller of a rotating body support device at one end in the axial direction of the rotating gantry, and a rear ring is disposed in contact with the roller at the other end in the axial direction of the rotating gantry. At least one intermediate ring is disposed in a position different in the axial direction of the gantry between the front and rear rings and in contact with the roller.

6 Claims, 15 Drawing Sheets

ROTATING IRRADIATION THERAPY APPARATUS

TECHNICAL FIELD

The present invention relates to a rotating irradiation therapy apparatus that irradiates an affected part of a body with an ion beam.

BACKGROUND ART

An ion beam irradiation system, which is a rotating irradiation therapy apparatus, treats cancer by irradiating an affected part of a patient's body with a proton beam, carbon ion beam, or other ion beam.

The ion beam irradiation system includes a rotating gantry, which is a rotating irradiation therapy apparatus. As disclosed, for instance, in Patent Document 1, the rotating gantry includes a front ring, a rear ring, and a gantry cylinder for connecting the front and rear rings. A beam transport device (beam path), which guides an ion beam, and an irradiation device (irradiation nozzle) are mounted on the gantry cylinder.

The mass of a beam transport system, which includes the aforementioned beam transport device and irradiation device, is used to generate a moment about a rotation axis of the rotating gantry. It is preferred that the moment about the rotation axis of the rotating gantry be minimized in a resting state. Therefore, the gantry cylinder includes a balance weight, which generates a moment that is oriented in a direction opposite to the direction of the moment generated by the beam transport system, and ensures that the moments about the rotation axis are balanced in the resting state.

The rotating gantry is supported at the positions of the front ring and rear ring by radial support devices having a plurality of freely-rotating rollers. The plurality of freely-rotating rollers, which are provided in each radial support device, are in contact with the front ring or rear ring. The rotating gantry rotates when some of the rollers are rotated by motors. The rotation of the rotating gantry orients the irradiation device so that an ion beam is incident on the affected part of the body.

In a rotating gantry for a particle beam therapy apparatus that is disclosed in Patent Document 2, a rear ring is supported by a support device with rollers, whereas a front ring is supported by a front support frame, which is mounted on a base section, via a swivel ring. The swivel ring is used so that the rear ring is rotatably mounted on the front support frame. The front support frame is mounted on a leg section, which is pivotally coupled by a pin to the base section. The pin is used so that the leg section can be tilted in the direction of the rotation axis of the rotating gantry. Therefore, the rear ring can also be tilted in the direction of the rotation axis of the rotating gantry. This configuration is employed to maintain the positional relationship between a bed and the rotating gantry.

A rotating gantry for a particle beam therapy apparatus is also referred to in Patent Document 3. This rotating gantry includes two rotating rings, which are supported by respective rollers. To maintain consistent rotation center position accuracy for a long period of time, a pair of drive rollers rotate at least either one of the rotating rings while the rotating ring is sandwiched between the drive rollers with both of its lateral surfaces brought into contact with the drive rollers.

Patent Document 4 also refers to a rotating gantry for a particle beam therapy apparatus. Rotating gantry members suitable particularly for irradiation with a carbon ion beam or other heavy particle beam are disclosed in this patent document. This rotating gantry includes a primary member, which is rotationally symmetric, and a secondary member, which is supported by the primary member to retain a bending magnet. A flexible, rigid member for providing a uniform amount of vertical displacement due to the bending magnet's own weight at all rotational angular positions is used as the secondary member to reduce the weight of the rotating gantry. In addition, the rotating gantry also includes a front ring and a rear ring. The weight of the rotating gantry is supported by a radial support device at a position of each ring. The employed design is such that either the front radial support device or the rear radial support device can be moved toward the rotation axis.

Patent Document 1: JP-A-11-47287
Patent Document 2: JP-A-2000-140134
Patent Document 3: Japanese Patent No. 3599995
Patent Document 4: JP-A-2004-148103

DISCLOSURE OF THE INVENTION

Problem to be Solved by the Invention

Before the start of medical treatment, the aforementioned particle beam therapy apparatus sets a charged particle beam irradiation position at an affected part of a patient's body. To provide increased therapy accuracy, it is preferred that the irradiation position remains unchanged without regard to the rotation of the rotating gantry.

In reality, however, the irradiation position moves three-dimensionally due to the rotation of the rotating gantry because of deflection caused by the weight of the rotating gantry and displacement of the rotating gantry rotation axis and roller rotation axis included in a rotating body support device. The center of such a three-dimensional movement of the irradiation position is called an isocenter (irradiation target center). It is demanded as a basic performance characteristic of a particle beam therapy apparatus that the three-dimensional movement of the irradiation position be confined within a sphere that is centered on the isocenter and several millimeters in diameter.

The above demand can be met, for instance, by using a gantry cylinder made of high-rigidity members for the purpose of reducing the amount of deformation of the rotating gantry. However, an increase in the rigidity of the rotating gantry increases the mass of the gantry cylinder. An increase in the mass of the rotating gantry increases the cost of particle beam therapy system introduction (e.g., the cost of particle beam therapy facility construction, the cost of apparatus transportation to a facility, and the cost of apparatus installation), thereby obstructing the development and spread of cancer treatment based on a particle beam.

For the above reason, it is demanded that a lightweight gantry exhibiting high irradiation accuracy (suffering from a minimum of three-dimensional movement of the irradiation position) be developed for use with a particle beam irradiation system. Further, a heavy particle beam such as a carbon ion beam causes greater damage to cancer cells than a proton beam and works effectively on cancer cells having a low oxygen concentration. It is therefore expected that cancer treatment based on a heavy particle beam be developed.

When a system for heavy particle beam irradiation is to be established, it is necessary that a rotating gantry for heavy particle beam irradiation be developed. The reason is that carbon ions and other heavy particles are heavier in mass than protons. When a heavy particle beam is to be incident on a predetermined spot, it is necessary that a larger-scale beam transport device and irradiation device be used than when a proton beam is used. The installation of a large-scale beam transport device and irradiation device requires the use of a large-size rotating gantry.

Consequently, the rotating gantry for the irradiation of a heavy particle beam is larger and heavier than that for the irradiation of a proton beam. As mentioned earlier, an increase in the mass of the rotating gantry increases the cost of particle beam therapy system introduction. Similarly, an increase in the size of the rotating gantry also increases the cost of therapy facility construction and the cost of apparatus installation, thereby increasing the cost of system introduction. For this reason, it is important that the rotating gantry to be developed for use with a heavy particle beam irradiation system be smaller in size and lighter in weight than the rotating gantry for a proton beam irradiation system.

An object of the present invention is to provide a small-size, lightweight rotating irradiation apparatus.

Problem to be Solved by the Invention

The above object is accomplished by a rotating irradiation therapy apparatus having a charged particle beam irradiation device, a beam transport device for introducing a charged particle beam to the irradiation device, a rotating body on which the beam transport device and the irradiation device are mounted, and rotating body support devices with freely-rotating rollers that come into contact with a circular member contained in the rotating body to support the rotating body, the rotating irradiation therapy apparatus including: a first circular member which comes into contact with the rollers of the rotating body support devices at one axial end of the rotating body; a second circular member which comes into contact with the rollers of the rotating body support devices at the other axial end of the rotating body; and an intermediate circular member which comes into contact with the rollers of at least one of the rotating body support devices at a different axial position of the rotating body between the first circular member and the second circular member.

The above object is accomplished by the rotating irradiation therapy apparatus, wherein the intermediate circular member is fixed to the rotating body by an intermediate circular member connection member contained in the rotating body; and wherein the mass of the intermediate circular member or the mass of the intermediate circular member connection member is varied in the circumferential direction of the rotating body to counteract at least part of a moment that rotates the rotating body about a rotation axis.

The above object is accomplished by the rotating irradiation therapy apparatus, wherein the intermediate circular member is fixed to the rotating body by the intermediate circular member connection member contained in the rotating body and the intermediate circular member or the intermediate circular member connection member serves to fix at least a part of the charged particle beam transport device to the rotating body.

The above object is accomplished by the rotating irradiation therapy apparatus, wherein the mass of the intermediate circular member or the mass of the intermediate circular member connection member is varied in the circumferential direction of the rotating body to counteract at least part of a moment that rotates the rotating body about a rotation axis.

The above object is accomplished by the rotating irradiation therapy apparatus, wherein the charged particle beam passes through a circular cylinder that is formed by the outer circumferential surface of the intermediate circular member which comes into contact with the rollers.

The above object is accomplished by the rotating irradiation therapy apparatus, wherein at least either one of the rotating body end support devices with freely-rotating rollers coming into contact with the first and second circular members can move toward the rotation axis of the rotating body; and wherein the rotating body intermediate support device with freely-rotating rollers coming into contact with the intermediate circular member can also move toward the rotation axis of the rotating body.

Advantages of the Invention

The present invention makes it possible to provide a lightweight rotating irradiation apparatus that exhibits high irradiation accuracy.

Other objects, features, and advantages of the present invention will become apparent upon reference to the following description of preferred embodiments of the present invention, which relates to the accompanying drawings.

BEST MODE FOR CARRYING OUT THE INVENTION

A first embodiment of the present invention will now be described with reference to FIGS. 1 to 13.

First Embodiment

First of all, a first configuration example of a rotating irradiation apparatus according to the first embodiment will be described with reference to FIGS. 1 to 5.

FIG. 1 is a side view illustrating the overall configuration of the rotating irradiation apparatus.

FIG. 2 is a rear view that is taken from cross-section line A-A in FIG. 1 to show the left side of FIG. 1.

FIG. 3 is a schematic diagram illustrating a beam transport system and a beam irradiation device, which are positioned in the rotating irradiation apparatus.

FIG. 4 is a side view obtained when a rotating section of the rotating irradiation apparatus is rotated from the position indicated in FIG. 1 by 180 degrees about a rotation axis.

FIG. 5 is a rear view that is taken from cross-section line A-A in FIG. 4 to show the left side of FIG. 4.

It should be noted that FIGS. 4 and 5 show only rollers 12 as component parts of a rotating body support device 16.

Referring to FIGS. 1 and 2, a rotating gantry 1 includes a front ring 3, which is positioned toward the front end (right side of FIG. 1) of a gantry cylinder 2 that is substantially cylindrical in shape; a rear ring 4, which is positioned toward the rear end (left side of FIG. 1); and an intermediate ring 5, which is positioned between the front ring 3 and the rear ring 4. The intermediate ring 5 is fixed to the gantry cylinder 2 by intermediate ring connection members 6a, 6b, and 6c. The gantry cylinder 2 is a cylindrically-shaped cylinder member. An irradiation device 8 is installed inside the gantry cylinder 2 so that a patient is irradiated with a charged particle beam, which is transported through a beam transport system 7 (described in detail with reference to FIG. 3).

The weight of the rotating gantry 1 is supported at the positions of the front ring 3, rear ring 4, and intermediate ring 5 by a plurality of rotatable rollers 12 of rotating body support devices 16a, 16b, and 16c. When the rotating gantry 1 rotates, the rollers 12 contained in the rotating body support devices 16a, 16b, and 16c rotate while maintaining contact with the outer circumferential surfaces of the front ring 3, rear ring 4, and intermediate ring 5. Therefore, the outer circumferential surfaces of the front, rear, and intermediate rings 3, 4, and 5 serve as the trajectory surfaces of the rollers 12.

FIGS. 1 and 2 show an example in which four rollers 12 are disposed for each ring. However, the number of rollers 12 coming into contact with each ring may be determined so that the contact surface pressure between a ring and a roller does not exceed a permissible value. In other words, the number of rollers 12 per ring is not limited to four.

Referring to FIG. 3, the beam transport system 7 in the rotating irradiation apparatus includes a bending magnet 9 for changing the direction of a charged particle beam, beam transport devices 10 (quadrupole magnet, steering magnet, and profile monitor included), and a vacuum duct 11. As shown in FIGS. 1 and 2, the present embodiment is configured so that the beam transport devices 10 and vacuum duct 11 are partially fixed to the gantry cylinder 2 by the intermediate ring 5 and intermediate ring connection member 6a. The reference numeral 8 denotes the irradiation device, which irradiates a patient with a charged particle beam. In other words, the intermediate ring connection member 6a shown in FIGS. 1 and 2 not only serves to fix the intermediate ring 5 to the gantry cylinder 2 but also serves to fix the beam transport devices 10 and vacuum duct 11 to the gantry cylinder.

As shown in FIG. 2, the intermediate ring connection member 6c is placed at a position that is rotated from the intermediate ring connection member 6a by 180 degrees about the rotating gantry's rotation axis. The intermediate ring connection member 6c is similar to the other intermediate ring connection members 6a, 6b in that it serves to fix the intermediate ring 5 to the gantry cylinder 2. In addition, the intermediate ring connection member 6c has a mass that is necessary for counteracting the moment about the rotating gantry's rotation axis, which arises mainly due to the mass of the bending magnet 9, beam transport devices 10, and irradiation device 8. In other words, the intermediate ring connection member 6c serves also as a counterbalance weight for canceling a rotational moment.

In the present embodiment, the outside diameter Rr (shown in FIG. 1) of the intermediate ring 5 is larger than the maximum turning radius Rg (shown in FIG. 1) of the beam transport system 7. The use of the intermediate ring 5 having such an outside diameter makes it possible to irradiate a patient with a particle beam even in a state (FIGS. 4 and 5) where the rotating gantry 1 is rotated from the state shown in shown in FIGS. 1 and 2 by 180 degrees about the rotation axis. In addition, the employed member allows the rotating gantry 1 to rotate by more than 180 degrees. More specifically, the rotating gantry 1 according to the present embodiment makes it possible to irradiate a patient with a particle beam from a wide range of rotation angles (0° to ±180° or more) without moving the patient. Therefore, the rotating irradiation apparatus is adaptable to various patient positions.

As shown in FIG. 1, the rotating body support devices 16a, 16b, and 16c each include a linear guide 17. The friction coefficient of the linear guide 17 is smaller than the friction coefficient acting on the contact surface between the rings (front ring 3, rear ring 4, and intermediate ring 5) and rollers 12. The linear guide 17 can freely move only in the rotation axis direction of the rotating gantry 1 and exhibits high torsional stiffness in a direction perpendicular to the rotation axis direction. The axial motion of the rotating gantry 1 is bound by a thrust support device (not shown). Therefore, a change in the axial positional relationship between the rotating gantry 1 and the rotating body support devices 16a, 16b, and 16c, which occurs due to rotation axis displacement of the rotating gantry 1 and rollers 12, is absorbed when the linear guide 17 moves in an axial direction.

FIG. 6 is a side view illustrating a second configuration example of the rotating irradiation apparatus according to the first embodiment of the present invention.

FIG. 7 is a rear view that is taken from cross-section line A-A in FIG. 6 to show the left side of FIG. 6.

As is the case with FIGS. 1 and 2, FIGS. 6 and 7 show only rollers 12 as component parts of a rotating body support device 16. The rotating body support device 16 supports the mass of the rotating gantry 1 at the positions of the rollers 12. As the rollers 12 are contained in the rotating body support device 16 in all the configuration examples in which the rollers 12 are shown, it is hereinafter assumed that the rotating body support device 16 supports the mass of the rotating gantry 1 at the positions of the rollers 12.

In the present configuration example, the mass of the intermediate ring 5 varies in circumferential direction because the intermediate ring 5 contains an additional mass 15. The mass of the intermediate ring 5 serves to counteract the moment about a rotation axis, which arises due, for instance, to the mass of the bending magnet 9, beam transport devices 10, and irradiation device 8, that is, serves as a counterbalance weight. The intermediate ring connection member 6c may also serve as a counterbalance weight in addition to the intermediate ring 5. Another alternative is to use the intermediate ring connection member 6c as a member (mass) that merely serves to fix the intermediate ring 5 to the gantry cylinder. When such a configuration is employed, the intermediate ring 5 and intermediate ring connection member 6 double as a counterbalance weight, thereby minimizing an increase in the mass that is caused by the installation of the intermediate ring 5 and intermediate ring connection member 6.

FIG. 8 is a side view illustrating a third configuration example of the rotating irradiation apparatus according to the first embodiment of the present invention.

FIG. 9 is a rear view that is taken from cross-section line A-A in FIG. 8 to show the left side of FIG. 8.

The configuration of the rotating irradiation apparatus shown in FIGS. 8 and 9 is similar to the one shown in FIGS. 1 and 2 in that the beam transport devices 10 and vacuum duct 11 are partially fixed to the gantry cylinder 2 by the intermediate ring 5 and intermediate ring connection member 6a. However, the configuration of the rotating irradiation apparatus shown in FIGS. 8 and 9 is different from the one shown in FIGS. 1 and 2 in that the former includes a counterbalance weight 13 for counteracting the moment about the rotating gantry's rotation axis, which arises due to the mass of the bending magnet 9, beam transport devices 10, and irradiation device 8. When this configuration is employed, the mass of the intermediate ring connection member 6c may be adjusted to have the intermediate ring connection member 6c perform part of the function of the counterbalance weight 13. Another alternative is to use the intermediate ring connection member 6c as a member (mass) that merely serves to fix the intermediate ring 5 to the gantry cylinder. When the intermediate ring connection member 6c performs part of the function of the counterbalance weight 13, the mass of the counterbalance weight 13 can be reduced, for instance, to increase the ease of counterbalance weight installation and adjustment.

FIG. 10 is a side view illustrating a fourth configuration example of the rotating irradiation apparatus according to the first embodiment of the present invention.

The rotating irradiation apparatus shown in FIG. 10 is configured so as to include two units of the intermediate ring 5 in the first configuration example, which is shown in FIGS. 1 to 3. In the configuration examples shown in FIGS. 1 to 9, one unit of the intermediate ring 5 is included so as to support the weight of the rotating gantry 1 at three axial points or three places (front ring 3, rear ring 4, and intermediate ring 5). In the present (fourth) configuration example, however, the deflection of the rotating gantry 1 is smaller than in the first configuration example because the weight of the rotating gantry 1 is supported at four axial points. Further, the weight of the rotating gantry 1 is supported at four places that differ in the axial direction (at the installation positions of the rollers 12 shown in FIG. 10). Therefore, the load supported by one rotating body support device is lower than in the first configuration example. This permits the use of smaller-size, simplified rotating body support devices. In the present configuration example, the intermediate ring connection member 6c serves as a counterbalance weight to counteract the moment about the rotation axis. However, the intermediate ring 5 may perform part of the function of the counterbalance weight as described in conjunction with the second configuration example. Another alternative is to use the counterbalance weight 13 shown in FIGS. 8 and 9 in addition to the intermediate ring connection member 6c as described in conjunction with the third configuration example.

FIG. 11 is a side view illustrating a fifth configuration example of the rotating irradiation apparatus according to the first embodiment of the present invention.

The configuration of the rotating irradiation apparatus shown in FIG. 11 differs from the first to fourth configuration examples in that the gantry cylinder is not substantially cylindrical in shape. More specifically, the gantry cylinder shown in the present configuration example includes the front ring 3, the rear ring 4, and a coupling steel pipe 14 for connecting the front ring 3 to the rear ring 4. This gantry cylinder has a lower rigidity than the gantry cylinder 2 that is shown in FIG. 1 and substantially cylindrical in shape, but can reduce the total mass of the rotating gantry. Further, the intermediate ring 5 is fixed to the gantry cylinder (front ring 3, rear ring 4, and coupling steel pipe 14) by the intermediate ring connection members 6a, 6b, and 6c. As is the case with the first to third configuration examples, the intermediate ring 5 and intermediate ring connection member 6a serve to partially fix the beam transport devices 10 and vacuum duct 11 to the gantry cylinder, whereas the intermediate ring connection member 6c functions as a counterbalance weight.

Even when the gantry cylinder includes the coupling steel pipe 14 as described in conjunction with the present configuration example, using the intermediate ring 5 so as to support the weight of the rotating gantry at three points makes it possible to provide a rotating irradiation apparatus that exhibits low deflection and high irradiation accuracy as is the case with the rotating gantry having a gantry cylinder that is substantially cylindrical in shape.

Referring to FIG. 11, the intermediate ring connection member 6c serves as a counterbalance weight. Alternatively, however, the intermediate ring 5 may function as a counterbalance weight as is the case with the second configuration example shown in FIGS. 6 and 7. Another alternative is to install a counterbalance weight in addition to the intermediate ring connection member 6c, as is the case with the third configuration example shown in FIGS. 8 and 9. Further, although one unit of the intermediate ring 5 is used in the configuration example shown in FIG. 11, installing two units of the intermediate ring 5 at different axial positions as is the case with the fourth configuration example shown in FIG. 10 ensures that the deflection caused by the weight of the rotating gantry is smaller than when one unit of the intermediate ring 5 is used.

FIGS. 12 and 13 illustrate a sixth configuration example of the rotating irradiation apparatus according to the first embodiment of the present invention. FIG. 12 is a side view. FIG. 13 is a diagram illustrating a beam transport system and a beam irradiation device positioned in the rotating irradiation apparatus that are included in the sixth configuration example.

In the beam transport system shown in FIG. 13, the vacuum duct 11, which is a trajectory of charged particles, is not positioned in parallel to the rotation axis. This beam transport system configuration is frequently used in a proton beam irradiation apparatus. FIG. 12 shows a rotating irradiation apparatus that is obtained by applying the first configuration example to the beam transport system shown in FIG. 13. Applying the above-described configuration to a proton beam therapy apparatus makes it possible to reduce the deflection of the rotating gantry 1, as is the case with the other configuration examples. Therefore, a rotating gantry for use with a proton beam therapy apparatus exhibiting high irradiation accuracy can be implemented.

The first to sixth configuration examples according to the first embodiment of the present invention, which have been described above, reduce the cost of rotating irradiation apparatus introduction and increase the number of people per year who receive particle beam therapy because they position the intermediate ring between the front ring and rear ring of the rotating gantry and allow radial support devices, namely, the rotating body support devices 16 including the rollers 12, to support the weight of the rotating gantry at the position of the intermediate ring in addition to the positions of the front ring and rear ring, cause the intermediate ring or a member connecting the intermediate ring to the gantry cylinder to double as a balance weight, and fix the charged particle beam transport devices to the gantry cylinder by the intermediate ring or the member connecting the intermediate ring to the gantry cylinder.

Second Embodiment

A configuration example of the rotating irradiation apparatus according to a second embodiment of the present invention will now be described with reference to FIGS. 14 and 15.

FIG. 14 is a side view illustrating a configuration example of the rotating irradiation apparatus according to the second embodiment of the present invention.

FIG. 15 is a rear view that is taken from cross-section line A-A in FIG. 14 to show the left side of FIG. 14.

As is the case with the configuration examples of the first embodiment, the rotating irradiation apparatus shown in FIGS. 14 and 15 is such that the intermediate ring connection member 6c not only serves to fix the intermediate ring 5 to the gantry cylinder 2 but also functions as a counterbalance weight. Further, the intermediate ring connection member 6a serves not only to fix the intermediate ring 5 to the gantry cylinder 2 but also to fix the beam transport devices 10 and vacuum duct 11 to the gantry cylinder.

However, the configuration example of the second embodiment differs from the configuration examples of the first embodiment in that the outside diameter Rr of the intermediate ring is smaller than the maximum turning radius Rg of the beam transport system 7. In the configuration example according to the second embodiment, therefore, the rotating gantry 1 cannot be rotated from the state shown in FIGS. 14 and 15 by 180 degrees about the rotation axis (rotated to the state shown in FIGS. 4 and 5, which depict a configuration example according to the first embodiment). Meanwhile, the above-described rotating irradiation apparatus, which is shown in FIGS. 14 and 15, permits the front ring 3, rear ring 4, and intermediate ring 5 to have the same outside diameter. This makes it possible to reduce the number of man-hours required for manufacture in contrast to a case where the employed rings differ in outside diameter. In addition, a building in which the rotating irradiation apparatus is installed can be reduced in size because the space in which the maximum turning radius Rg passes is limited.

In the present configuration example, the intermediate ring connection member 6c functions as a counterbalance weight. In the present embodiment, however, the intermediate ring 5 may function as a counterbalance weight as is the case with the second and third configuration examples according to the first embodiment. Further, as another alternative, a counterbalance weight 13 may be additionally employed. Furthermore, the present embodiment may use two or more units of the intermediate ring 5, as is the case with the fourth configuration example described in conjunction with the first embodiment. Although the gantry cylinder 2 included in the present configuration example is substantially cylindrical in shape, the present embodiment may also use a gantry cylinder 2 that includes a coupling steel pipe as is the case with the fifth configuration example described in conjunction with the first embodiment. Moreover, the configuration example according to the present embodiment can also be applied to a beam transport system that is represented by the sixth configuration example described in conjunction with the first embodiment and frequently used with a proton beam therapy apparatus. Such application makes it possible to implement a lightweight rotating irradiation apparatus that exhibits high irradiation accuracy.

The present embodiment reduces the cost of rotating irradiation apparatus introduction and increases the number of people per year who receive particle beam therapy because it positions the intermediate ring between the front ring and rear ring of the rotating gantry and allows radial support devices, namely, the rotating body support devices 16 including the rollers 12, to support the weight of the rotating gantry at the position of the intermediate ring in addition to the positions of the front ring and rear ring, causes the intermediate ring or a member connecting the intermediate ring to the gantry cylinder to function as a balance weight, and fixes the charged particle beam transport devices to the gantry cylinder by the intermediate ring or the member connecting the intermediate ring to the gantry cylinder.

While the present invention has been described in terms of preferred embodiments, persons of skill in the art will appreciate that the present invention is not limited to those preferred embodiments, and that various changes and modifications may be made without departing from the spirit and scope of the appended claims.

Figure 1:
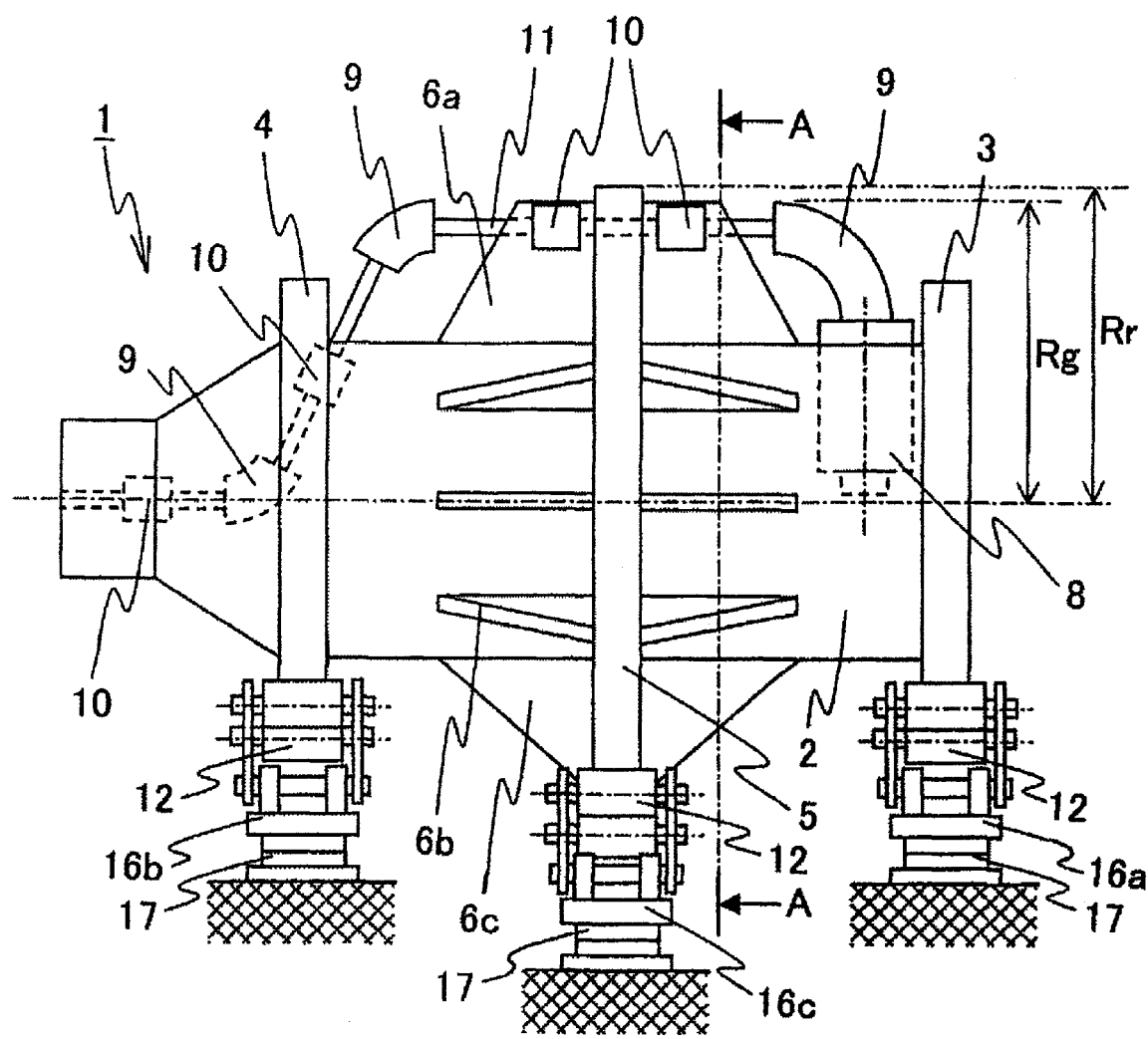
FIG. 1 is a side view illustrating a first configuration example of a rotating irradiation apparatus according to a first embodiment of the present invention.
Figure 2:
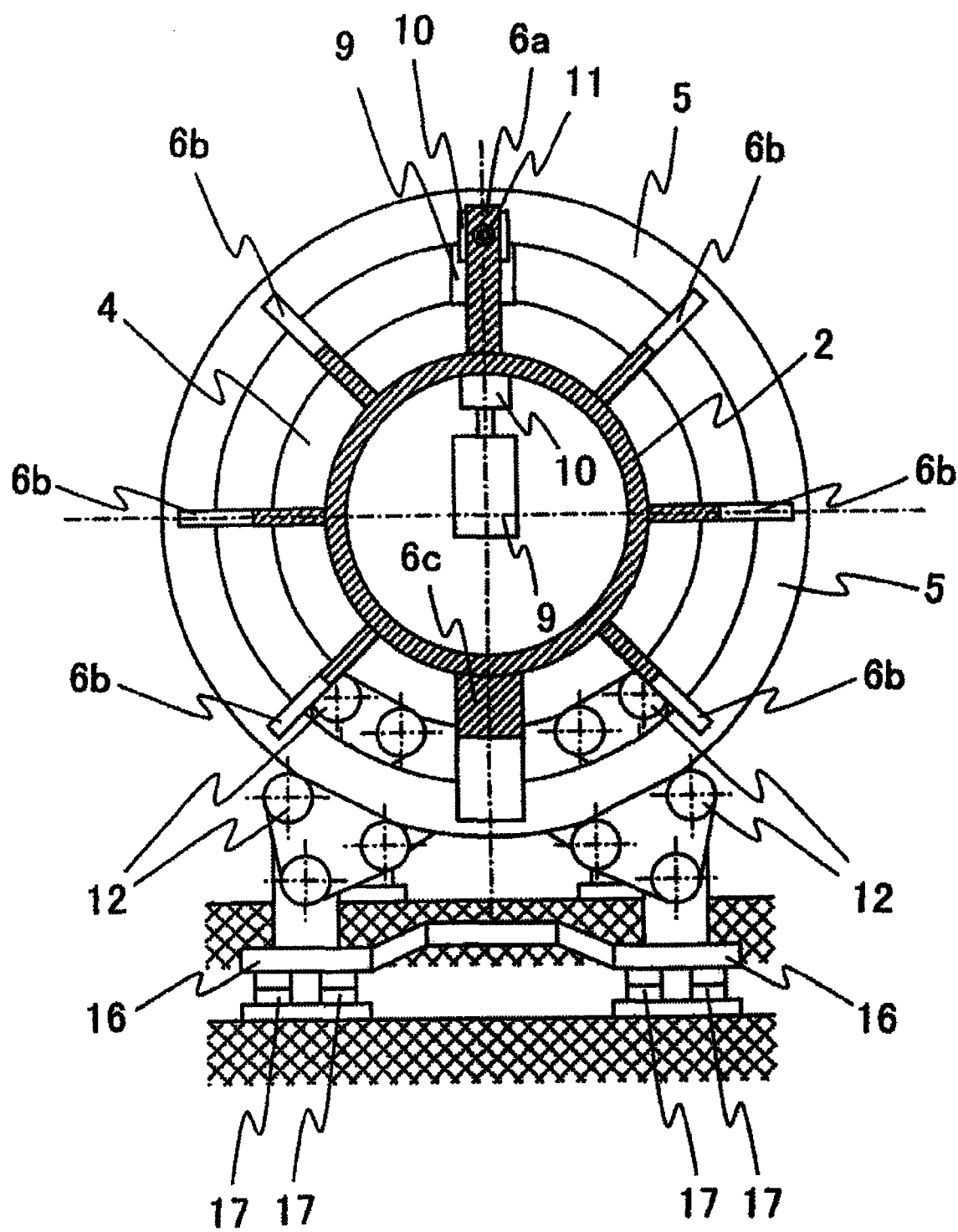
FIG. 2 is a rear cross-sectional view that is taken from line A-A in FIG. 1 to illustrate the first configuration example of the rotating irradiation apparatus according to the first embodiment of the present invention.
Figure 3:
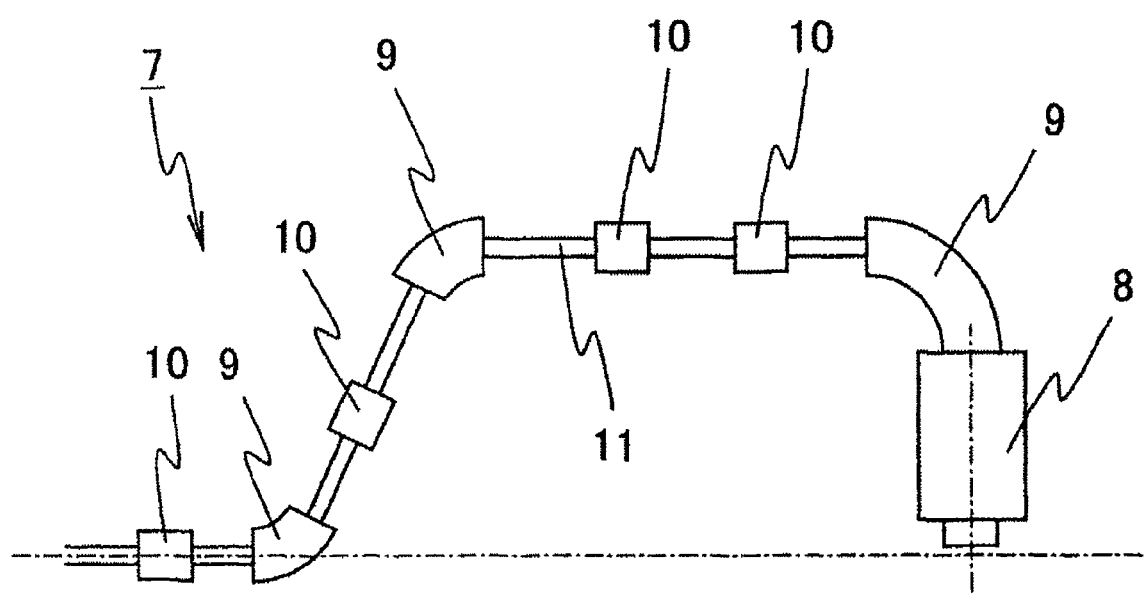
FIG. 3 is a side view illustrating a beam transport system that is included in the first configuration example of the rotating irradiation apparatus according to the first embodiment of the present invention.
Figure 4:
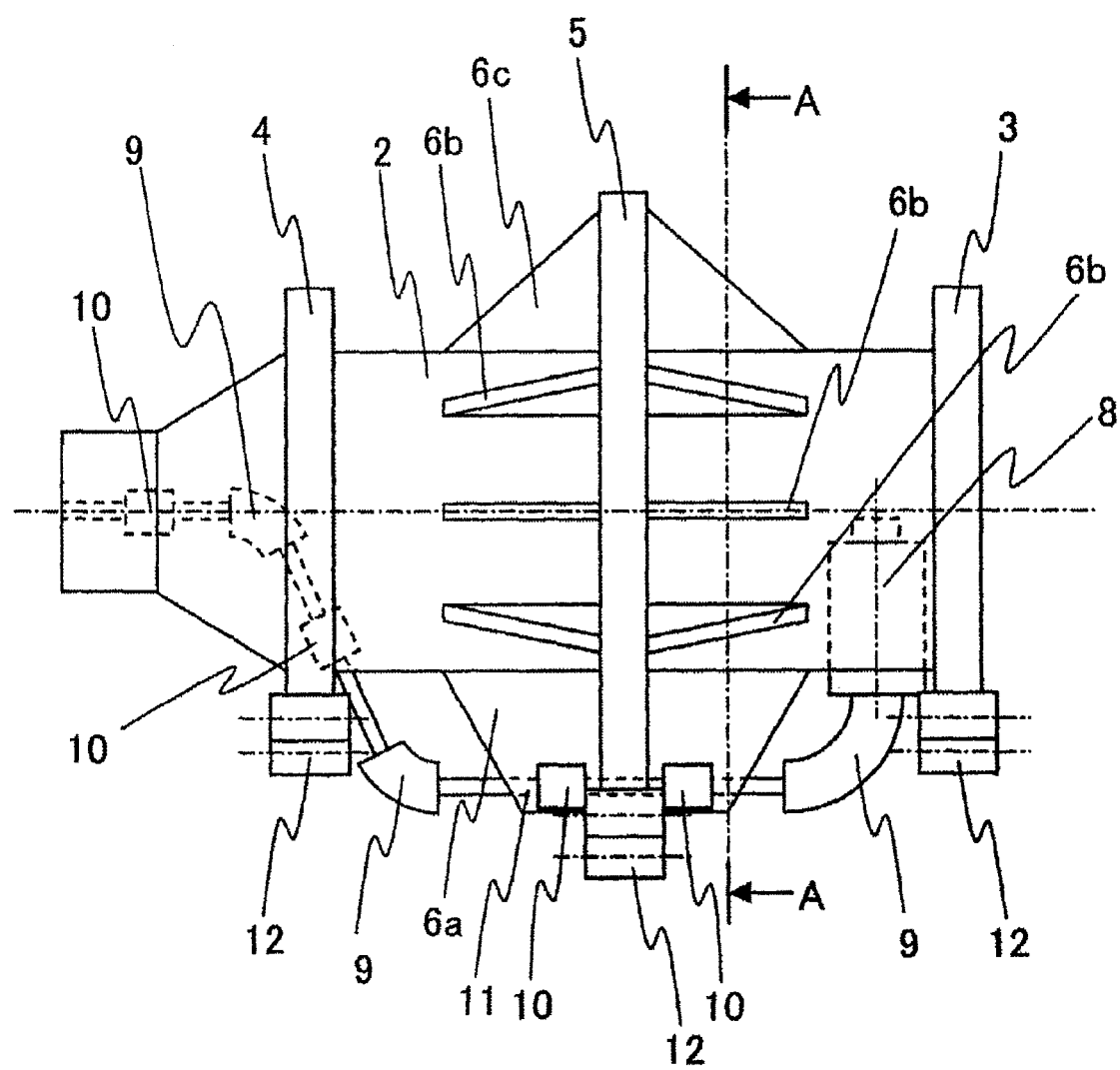
FIG. 4 is a side view that illustrates the first configuration example of the rotating irradiation apparatus according to the first embodiment of the present invention and is obtained when the rotating irradiation apparatus is rotated 180 degrees from the state indicated in FIG. 1.
Figure 5:
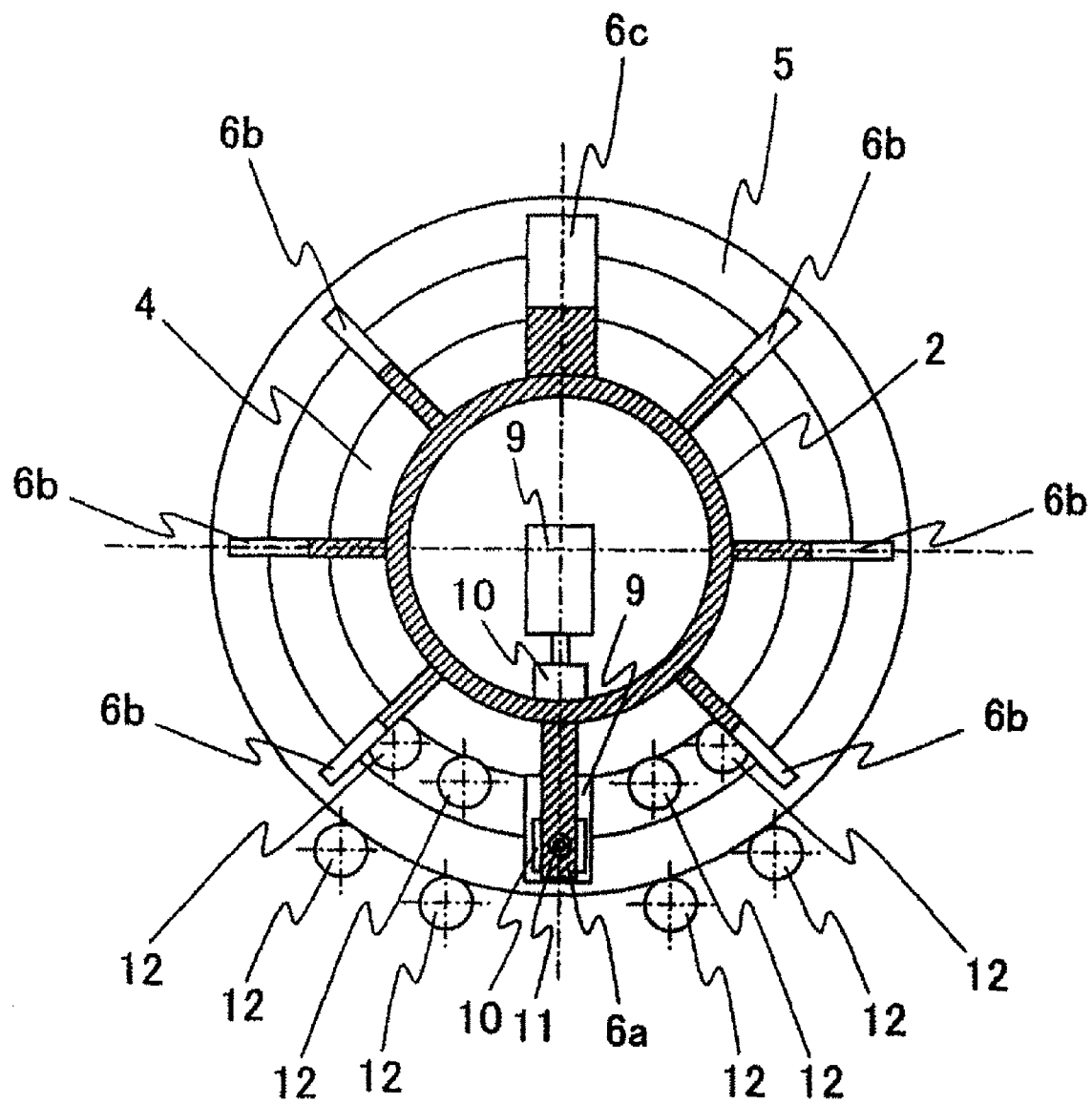
FIG. 5 is a rear cross-sectional view that is taken from line A-A in FIG. 4 to illustrate the first configuration example of the rotating irradiation apparatus according to the first embodiment of the present invention and obtained when the rotating irradiation apparatus is rotated 180 degrees from the state indicated in FIG. 1.
Figure 6:
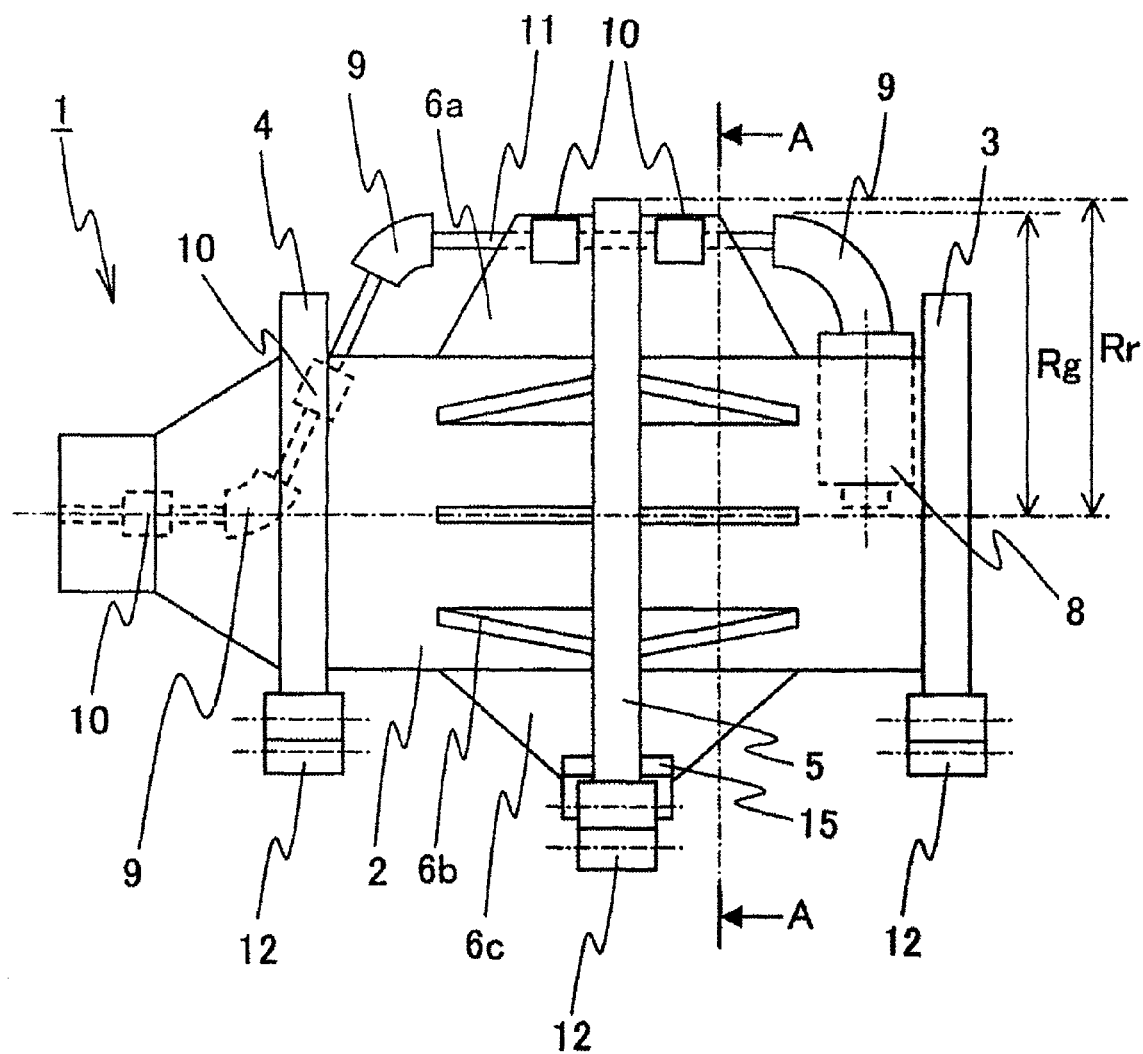
FIG. 6 is a side view illustrating a second configuration example of the rotating irradiation apparatus according to the first embodiment of the present invention.
Figure 7:
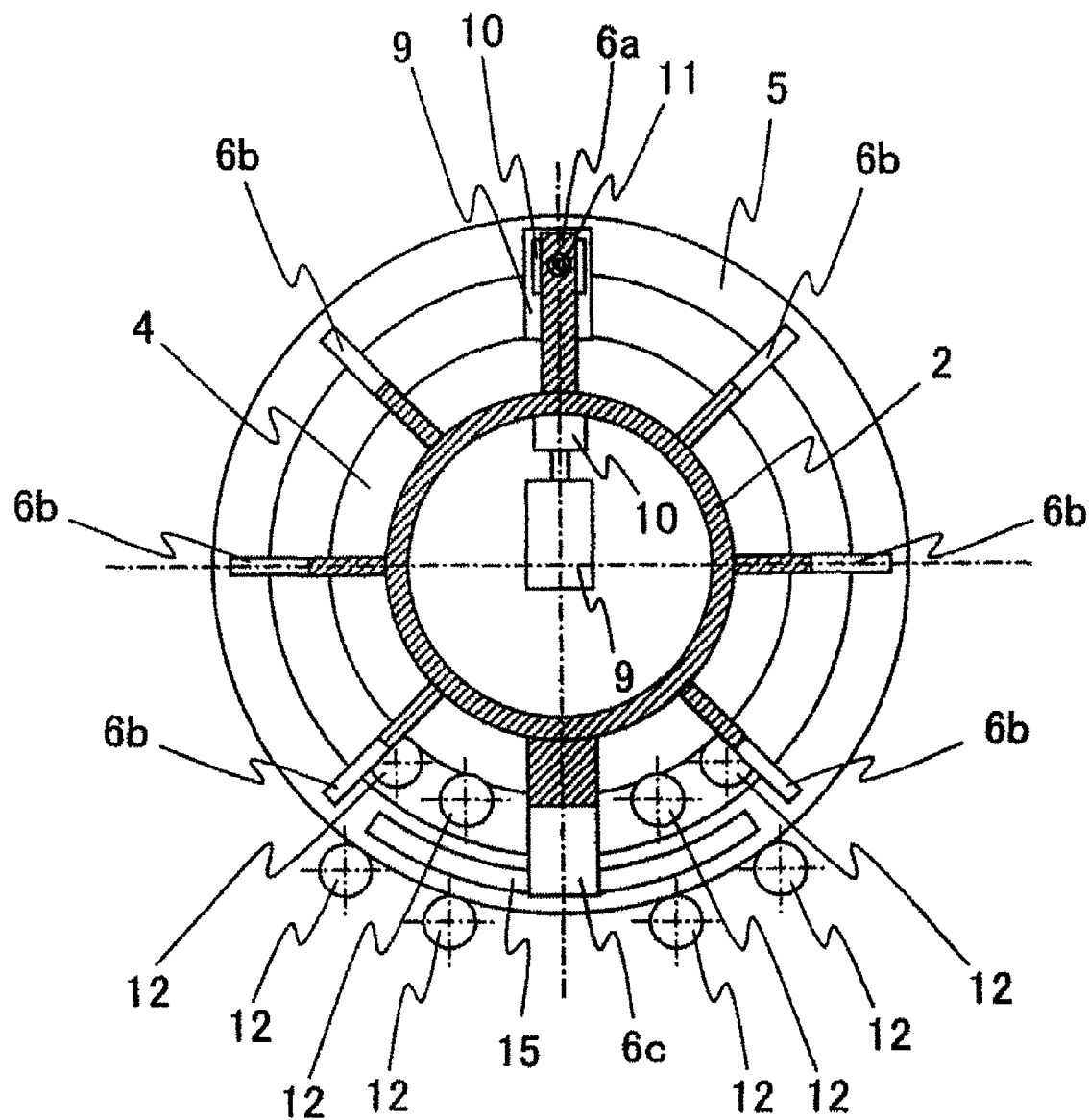
FIG. 7 is a rear cross-sectional view that is taken from line A-A in FIG. 6 to illustrate the second configuration example of the rotating irradiation apparatus according to the first embodiment of the present invention.
Figure 8:
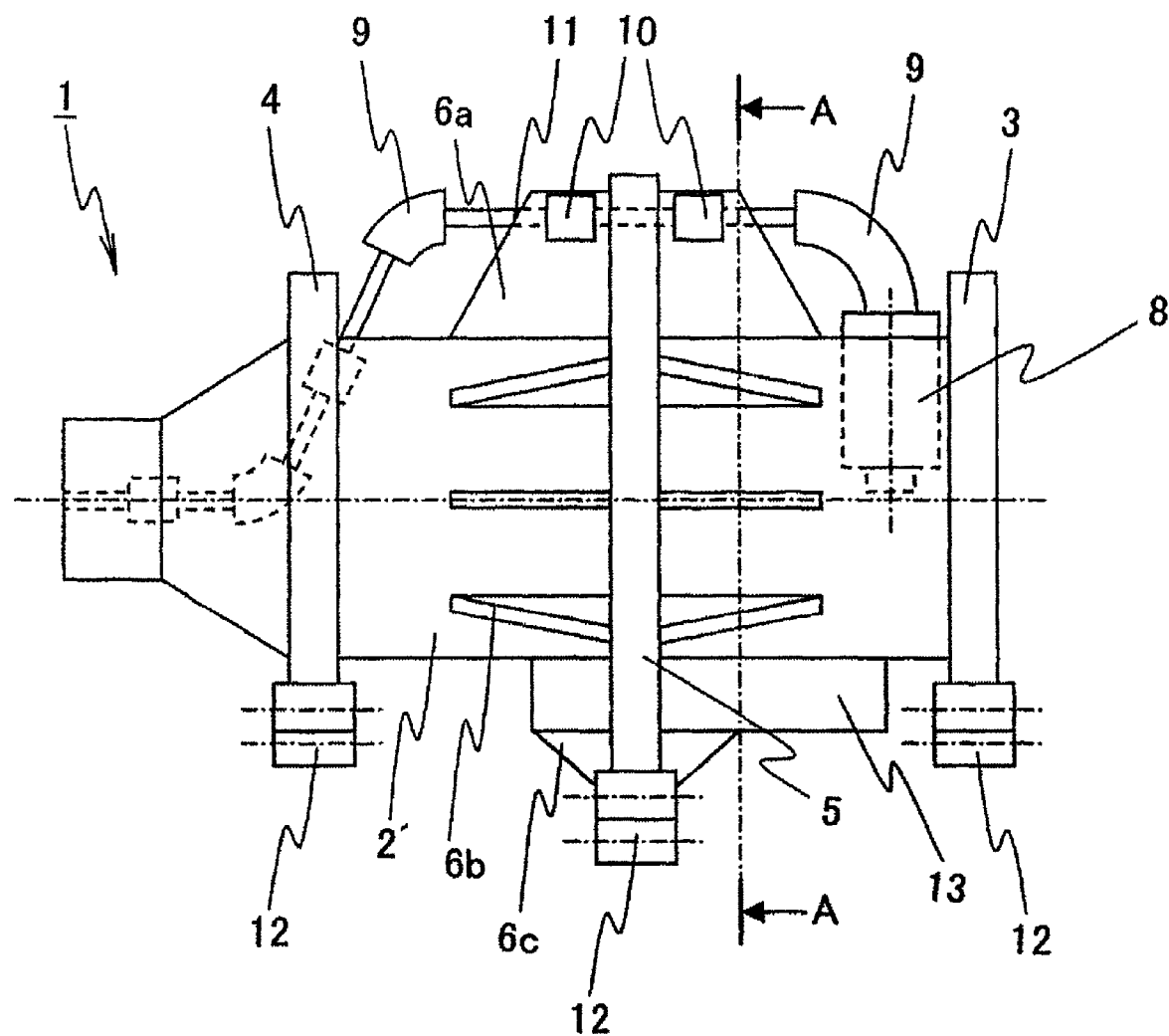
FIG. 8 is a side view illustrating a third configuration example of the rotating irradiation apparatus according to the first embodiment of the present invention.
Figure 9:
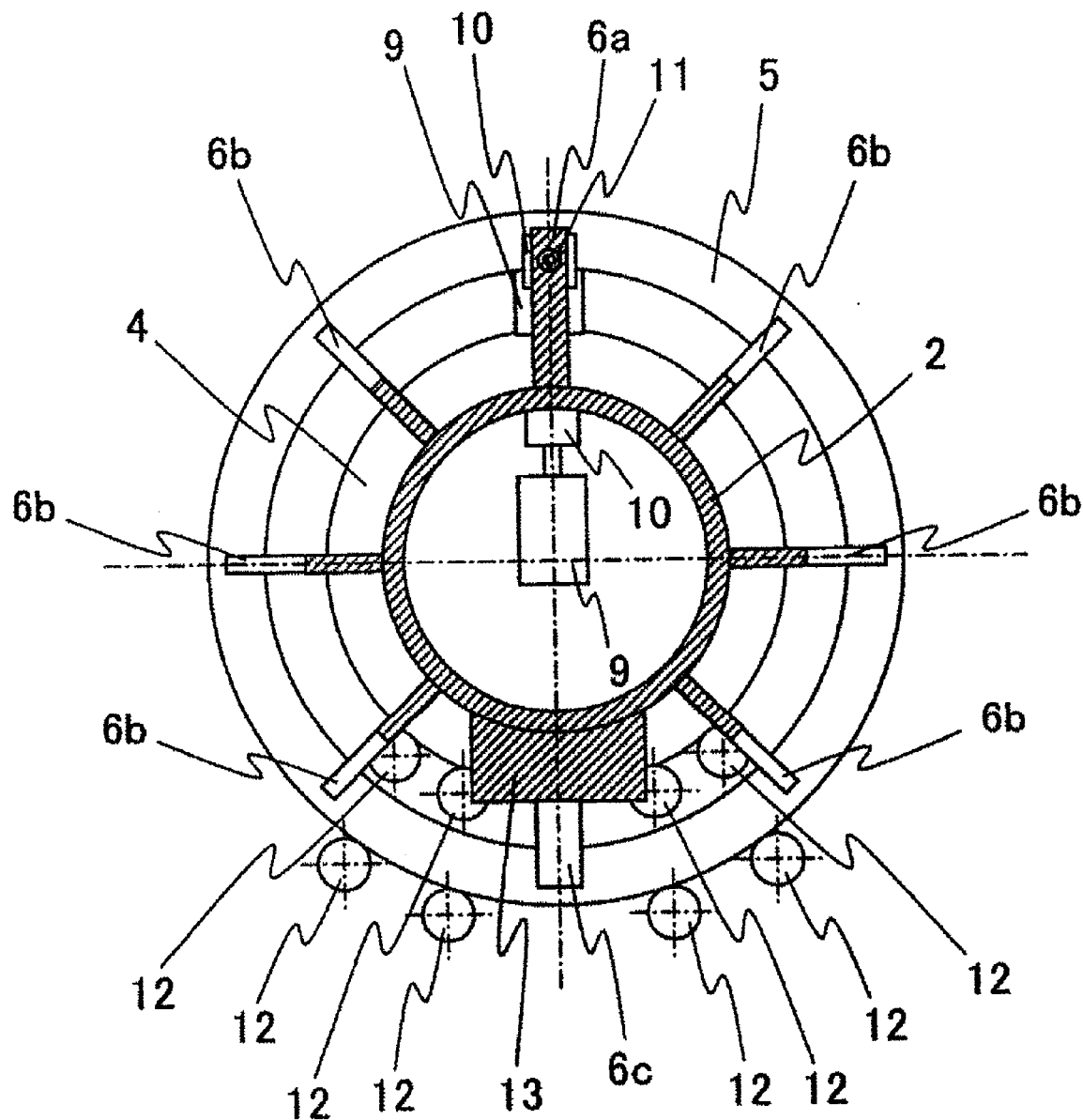
FIG. 9 is a rear cross-sectional view that is taken from line A-A in FIG. 8 to illustrate the third configuration example of the rotating irradiation apparatus according to the first embodiment of the present invention.
Figure 10:
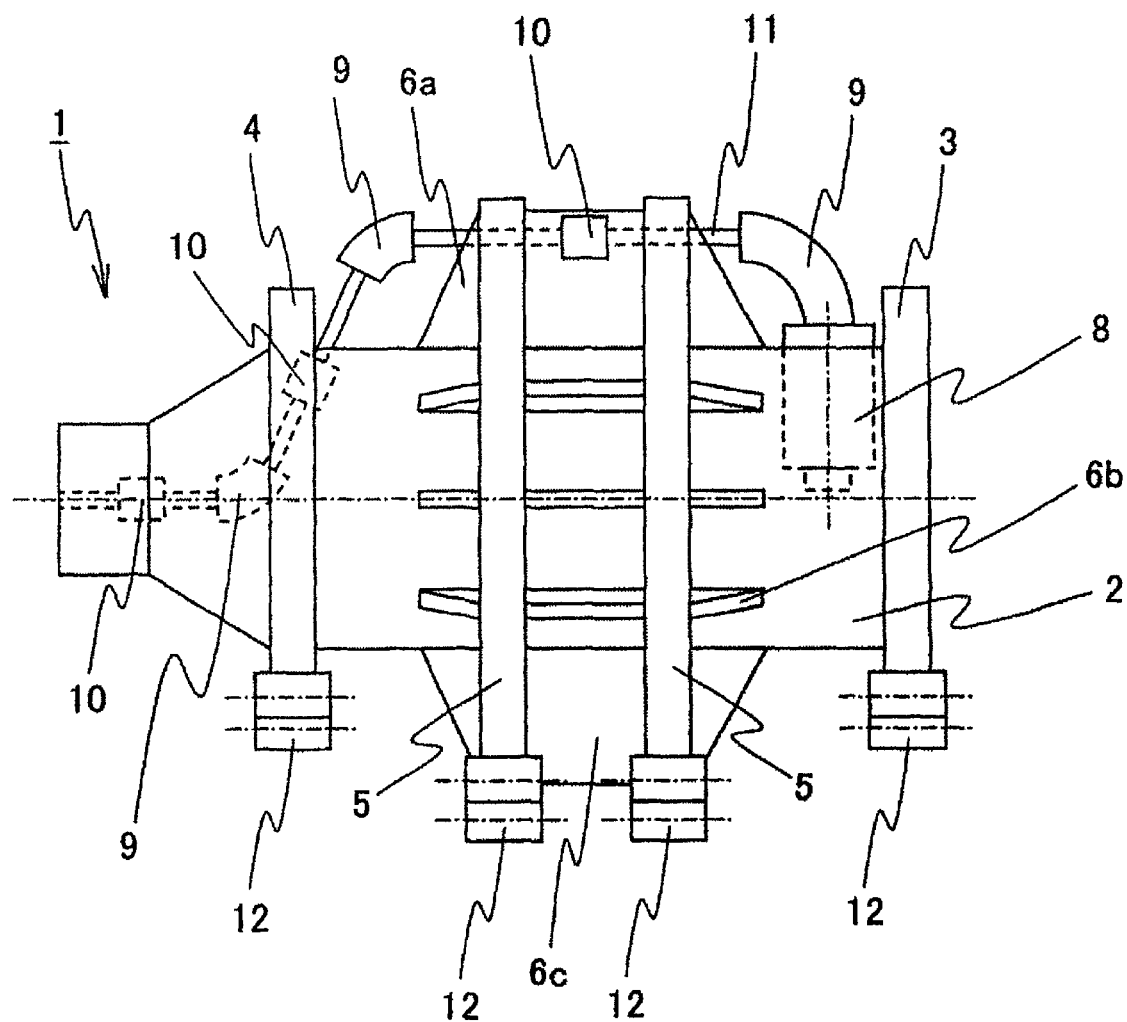
FIG. 10 is a side view illustrating a fourth configuration example of the rotating irradiation apparatus according to the first embodiment of the present invention.
Figure 11:
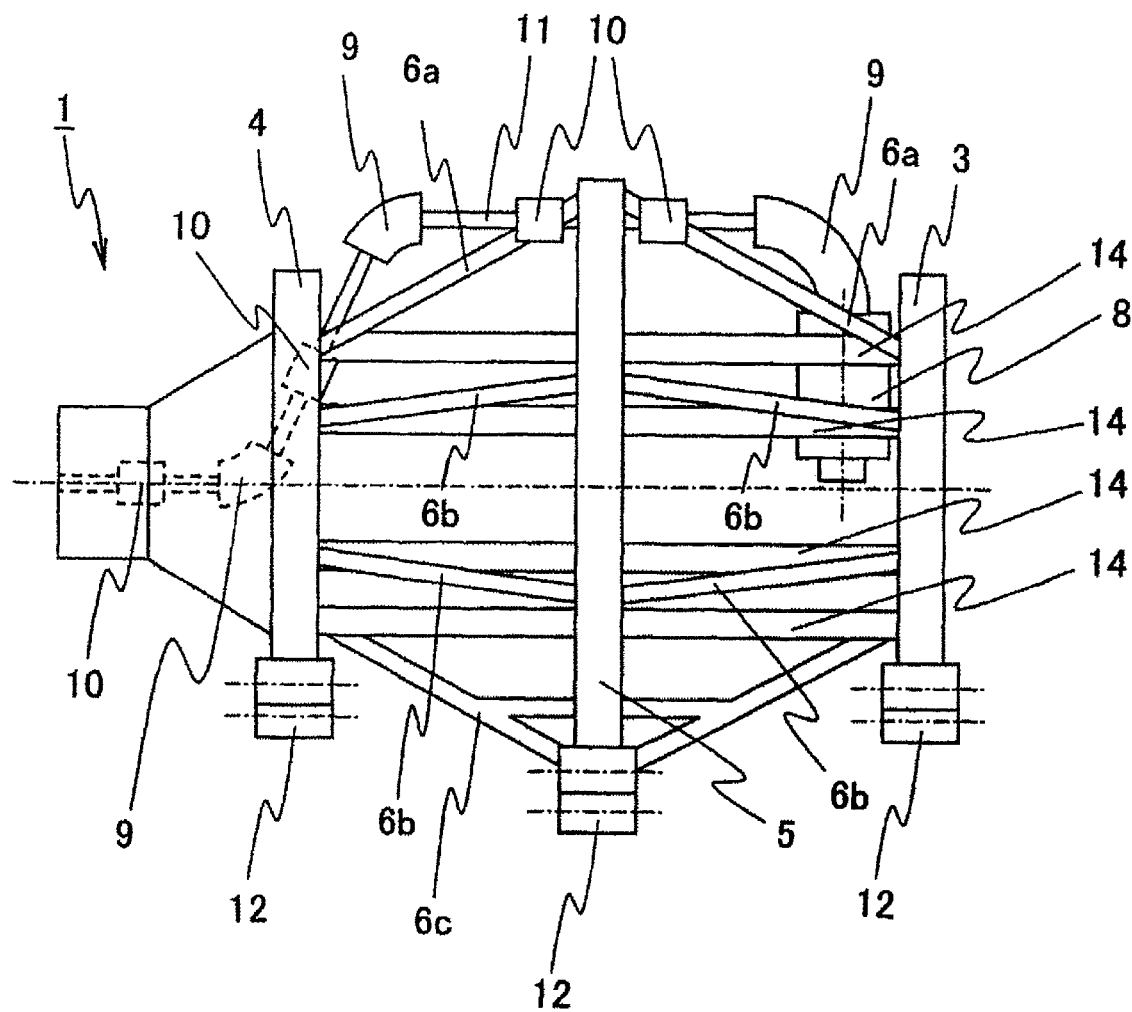
FIG. 11 is a side view illustrating a fifth configuration example of the rotating irradiation apparatus according to the first embodiment of the present invention.
Figure 12:
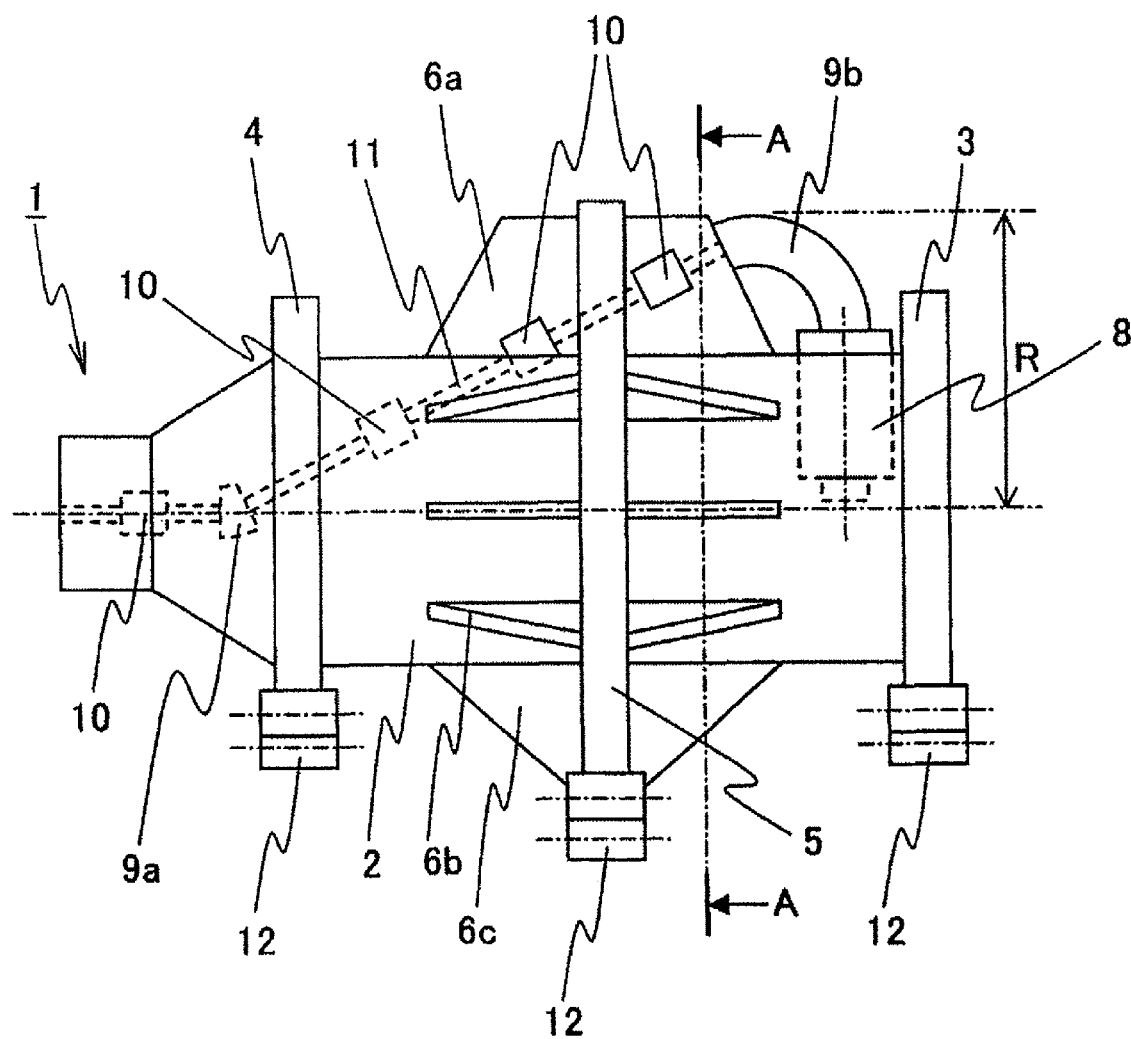
FIG. 12 is a side view illustrating a sixth configuration example of the rotating irradiation apparatus according to the first embodiment of the present invention.
Figure 13:
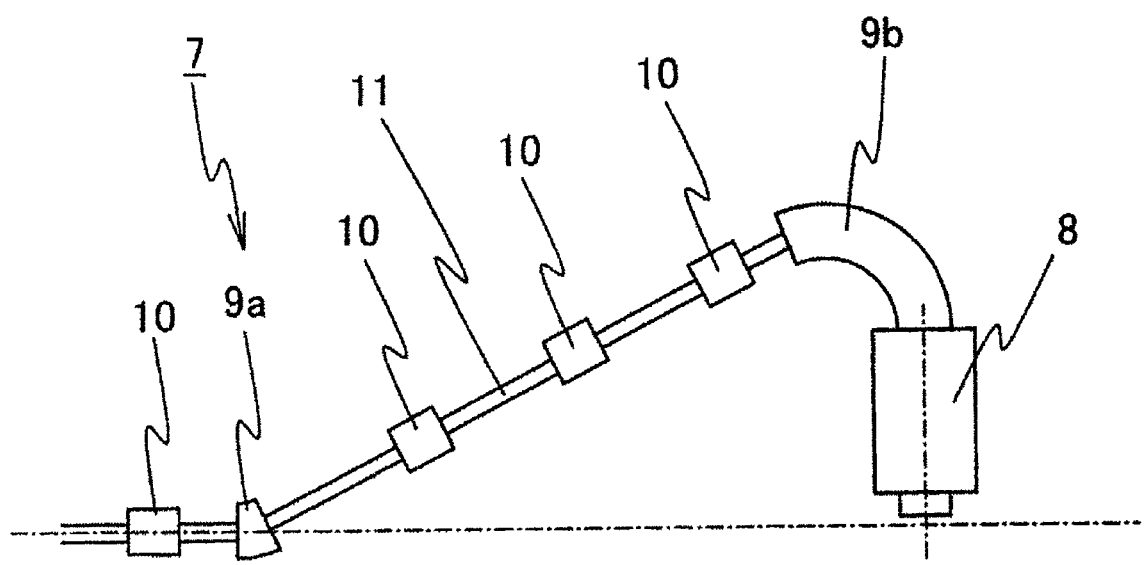
FIG. 13 is a view illustrating a beam transport system that is included in the sixth configuration example of the rotating irradiation apparatus according to the first embodiment of the present invention.
Figure 14:
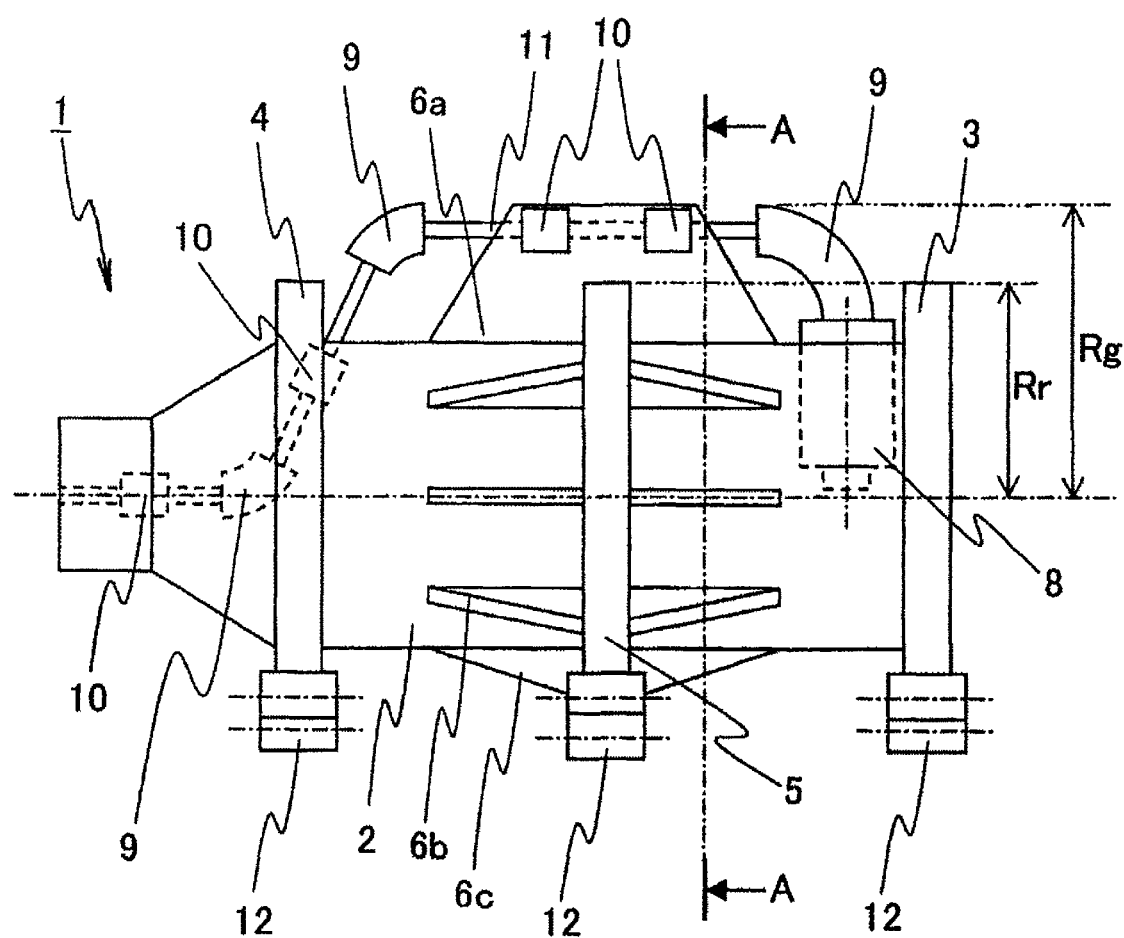
FIG. 14 is a side view illustrating a configuration example of the rotating irradiation apparatus according to a second embodiment of the present invention.
Figure 15:
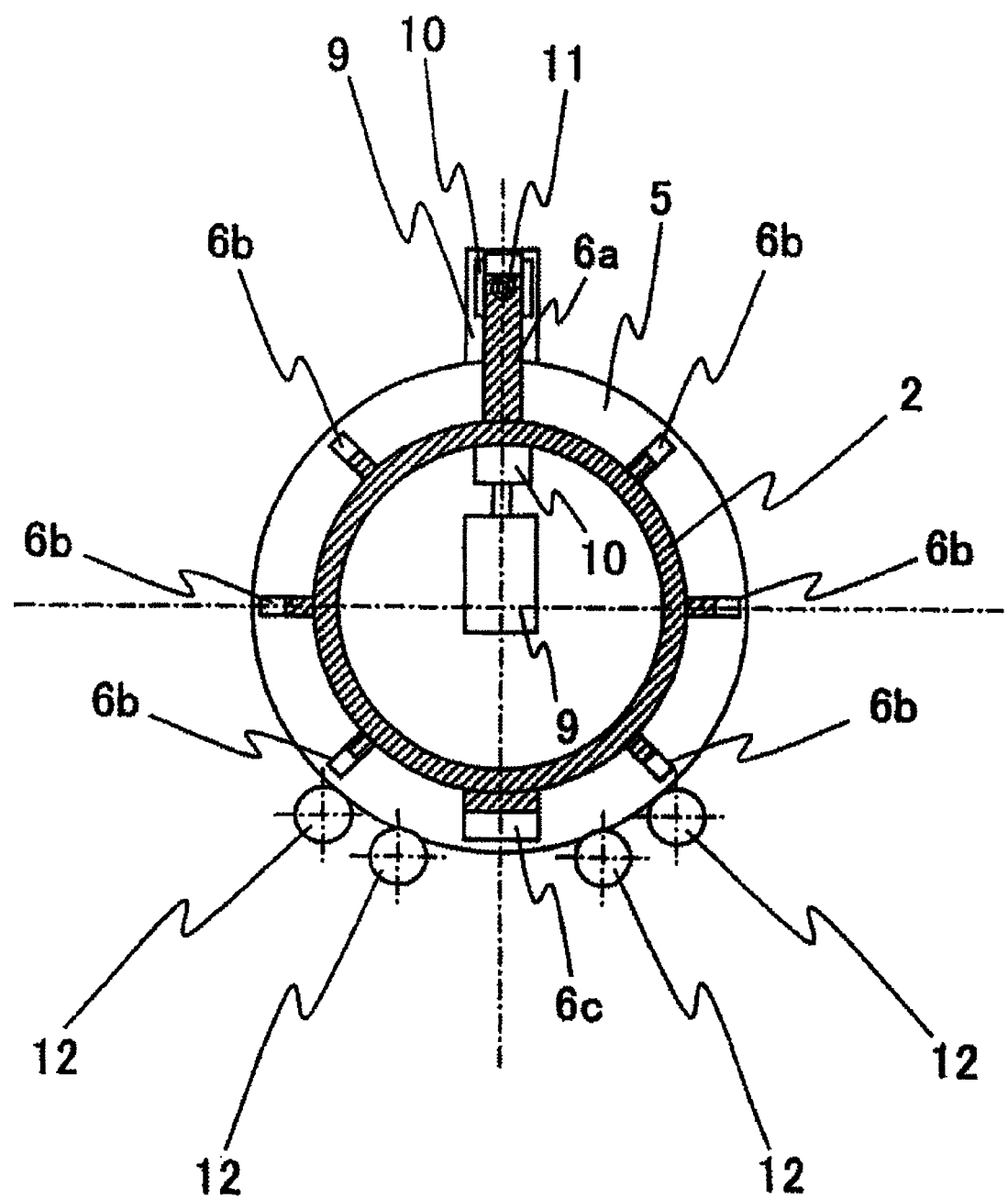
FIG. 15 is a rear cross-sectional view that is taken from line A-A in FIG. 14 to illustrate a configuration example of the rotating irradiation apparatus according to the second embodiment of the present invention.

The invention claimed is:

1. A rotating irradiation therapy apparatus having a charged particle beam irradiation device, a beam transport device for introducing a charged particle beam to the irradiation device, a rotating body on which the beam transport device and the irradiation device are mounted, and rotating body support devices with freely-rotating rollers that come into contact with a circular member contained in the rotating body to support the rotating body, the rotating irradiation therapy apparatus comprising:

a first circular member which comes into contact with the rollers of the rotating body support devices at one axial end of the rotating body;

a second circular member which comes into contact with the rollers of the rotating body support devices at the other axial end of the rotating body; and an intermediate circular member which comes into contact with the rollers of at least one of the rotating body support devices at a different axial position of the rotating body between the first circular member and the second circular member.

2. The rotating irradiation therapy apparatus according to claim 1, wherein the intermediate circular member is fixed to the rotating body by an intermediate circular member connection member contained in the rotating body; and wherein the mass of the intermediate circular member or the mass of the intermediate circular member connection member is varied in the circumferential direction of the rotating body to counteract at least part of a moment that rotates the rotating body about a rotation axis.

3. The rotating irradiation therapy apparatus according to claim 1, wherein the intermediate circular member is fixed to the rotating body by the intermediate circular member connection member contained in the rotating body and the intermediate circular member or the intermediate circular member connection member serves to fix at least a part of the charged particle beam transport device to the rotating body.

4. The rotating irradiation therapy apparatus according to claim 3, wherein the mass of the intermediate circular member or the mass of the intermediate circular member connection member is varied in the circumferential direction of the rotating body to counteract at least part of a moment that rotates the rotating body about a rotation axis.

5. The rotating irradiation therapy apparatus according to claim 1, wherein the charged particle beam passes through a circular cylinder that is formed by the outer circumferential surface of the intermediate circular member which comes into contact with the rollers.

6. The rotating irradiation therapy apparatus according to claim 1, wherein at least either one of the rotating body end support devices with freely-rotating rollers coming into contact with the first and second circular members can move toward the rotation axis of the rotating body; and wherein the rotating body intermediate support device with freely-rotating rollers coming into contact with the intermediate circular member can also move toward the rotation axis of the rotating body.

* * * * *